(12) United States Patent
Bolton

(10) Patent No.: US 7,223,391 B2
(45) Date of Patent: May 29, 2007

(54) METHOD FOR TREATING MAMMALS WITH MODIFIED MAMMALIAN BLOOD

(75) Inventor: Anthony E. Bolton, Ontario (CA)

(73) Assignee: Vasogen Ireland Limited, Shannon, County Clare (IE)

( * ) Notice: Subject to any disclaimer, the term of this patent is extended or adjusted under 35 U.S.C. 154(b) by 0 days.

(21) Appl. No.: 11/150,084

(22) Filed: Jun. 10, 2005

(65) Prior Publication Data

US 2005/0238623 A1    Oct. 27, 2005

Related U.S. Application Data

(63) Continuation of application No. 09/564,853, filed on May 5, 2000, now Pat. No. 6,986,888.

(30) Foreign Application Priority Data

May 6, 1999   (CA)   ..................... 2271190

(51) Int. Cl.
   *A01N 39/00*   (2006.01)
   *A01N 35/14*   (2006.01)
   *C12N 5/06*    (2006.01)

(52) U.S. Cl. ................. 424/93.7; 424/278.1; 424/529; 424/613; 435/372; 435/375; 435/377

(58) Field of Classification Search ............... 424/613, 424/810, 93.21, 278.1
   See application file for complete search history.

(56) References Cited

U.S. PATENT DOCUMENTS

| 4,968,483 A | 11/1990 | Mueller et al. |
| 5,591,457 A | 1/1997 | Bolton |
| 5,834,030 A | 11/1998 | Bolton |
| 5,980,954 A | 11/1999 | Bolton |
| 6,136,308 A | 10/2000 | Tremblay et al. |
| 6,572,895 B2 * | 6/2003 | Smith et al. ................. 424/529 |

FOREIGN PATENT DOCUMENTS

| WO | WO 96/34613 | 11/1996 |
| WO | WO 98/07436 | 2/1998 |
| WO | WO 99/13890 | 3/1999 |
| WO | WO 00/29003 | 5/2000 |
| WO | WO 00/62788 | 10/2000 |

OTHER PUBLICATIONS

Sweeney et al. *J. Leukoc. Biol.* 62(4):517-23 (Oct. 1997).
The Merck Manual of Diagnosis and Therapy, Seventeenth Edition, 1999, pp. 416-122 and pp. 1654-1658.
Van Noort et al. *International Review of Cytology* 178:127-205 (1998).

* cited by examiner

*Primary Examiner*—Christina Chan
*Assistant Examiner*—Phuong Huynh
(74) *Attorney, Agent, or Firm*—Foley & Lardner LLP

(57) ABSTRACT

An improved method for treating or preventing a pathological condition in a mammalian subject in which modified mammalian blood is administered to the subject. The method comprises administering to the subject from two to four aliquots of modified mammalian blood, with the administration of any pair of consecutive treatments either being on consecutive days or being separated by a rest period of 1 to 21 days. The treatment is useful for treating or preventing a wide range of pathological conditions in which modified mammalian blood is effective, including preconditioning a mammalian subject to better withstand the adverse effects of ischemic stress, atherosclerosis and rheumatoid arthritis.

5 Claims, 6 Drawing Sheets

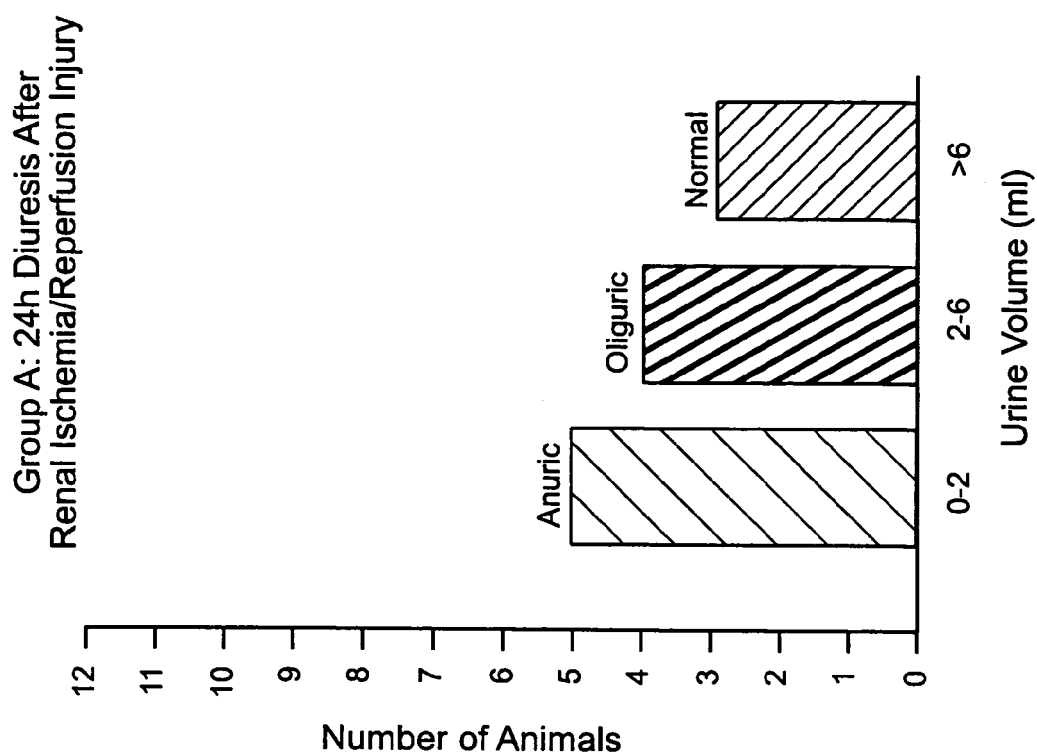
FIG._2
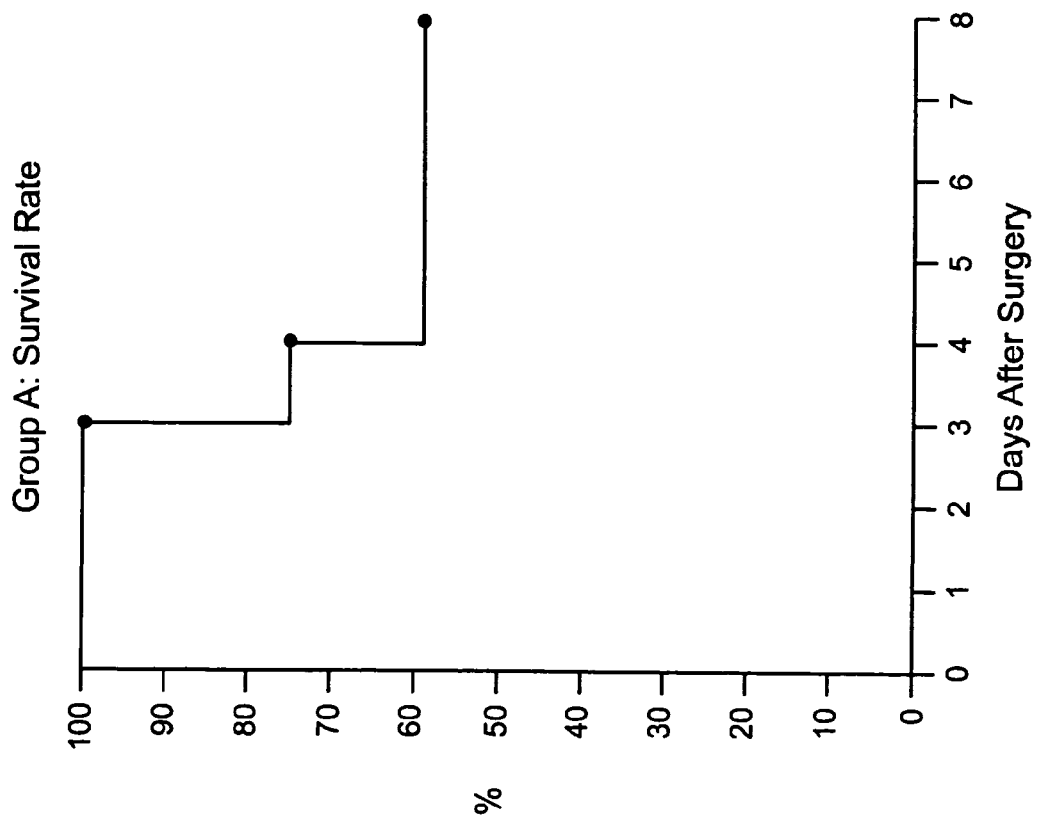
FIG._1

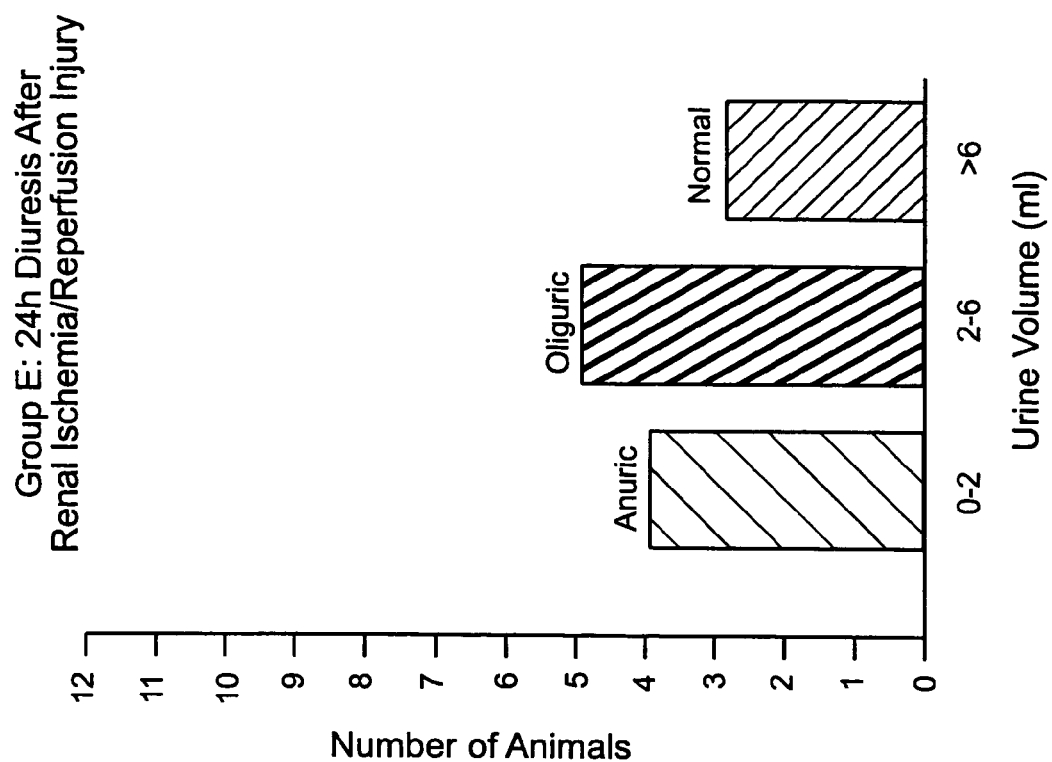
FIG._4
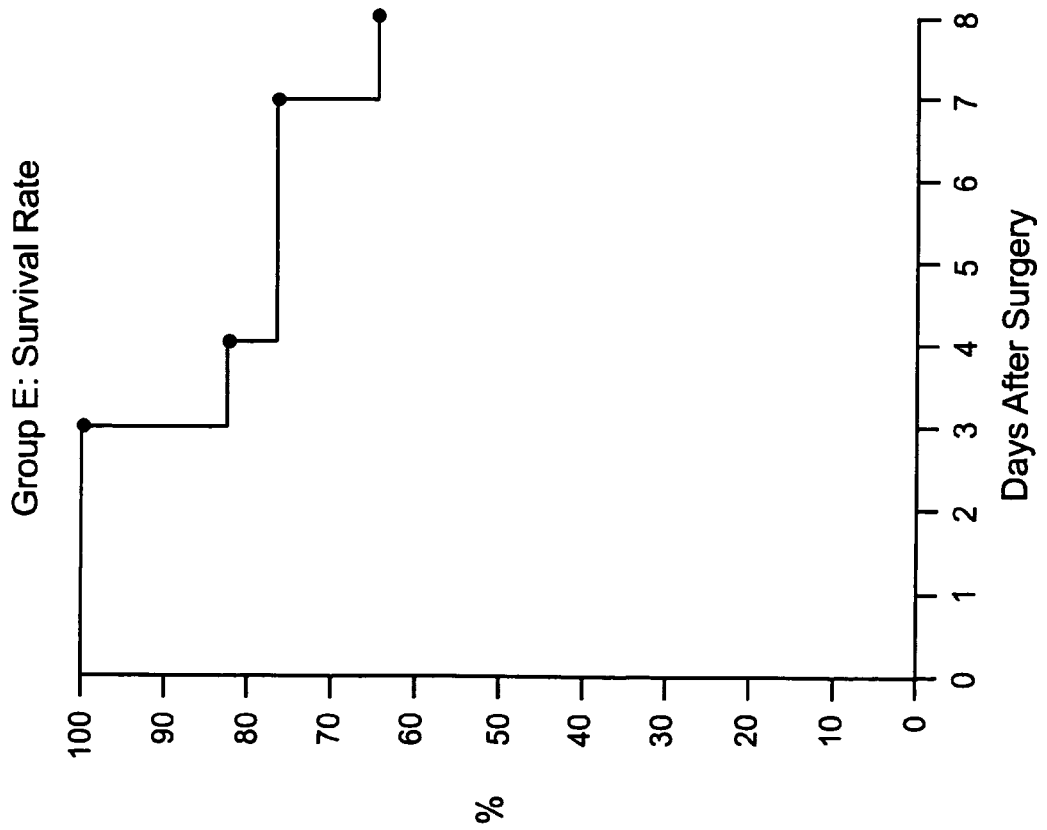
FIG._3

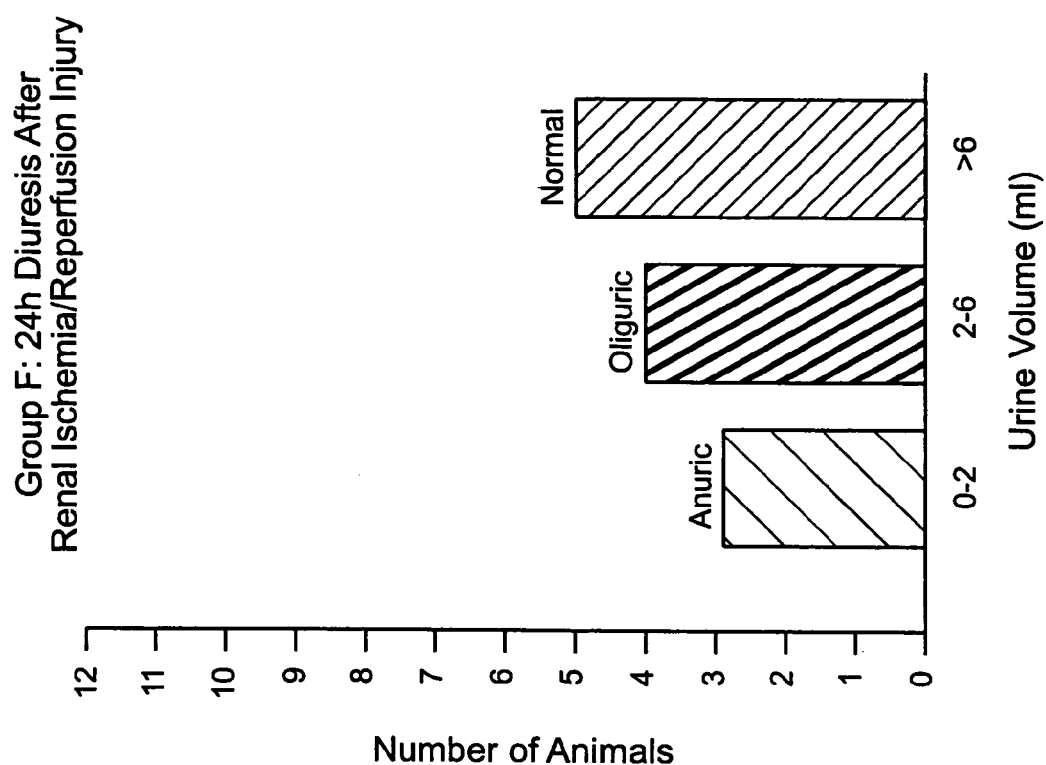
FIG._6
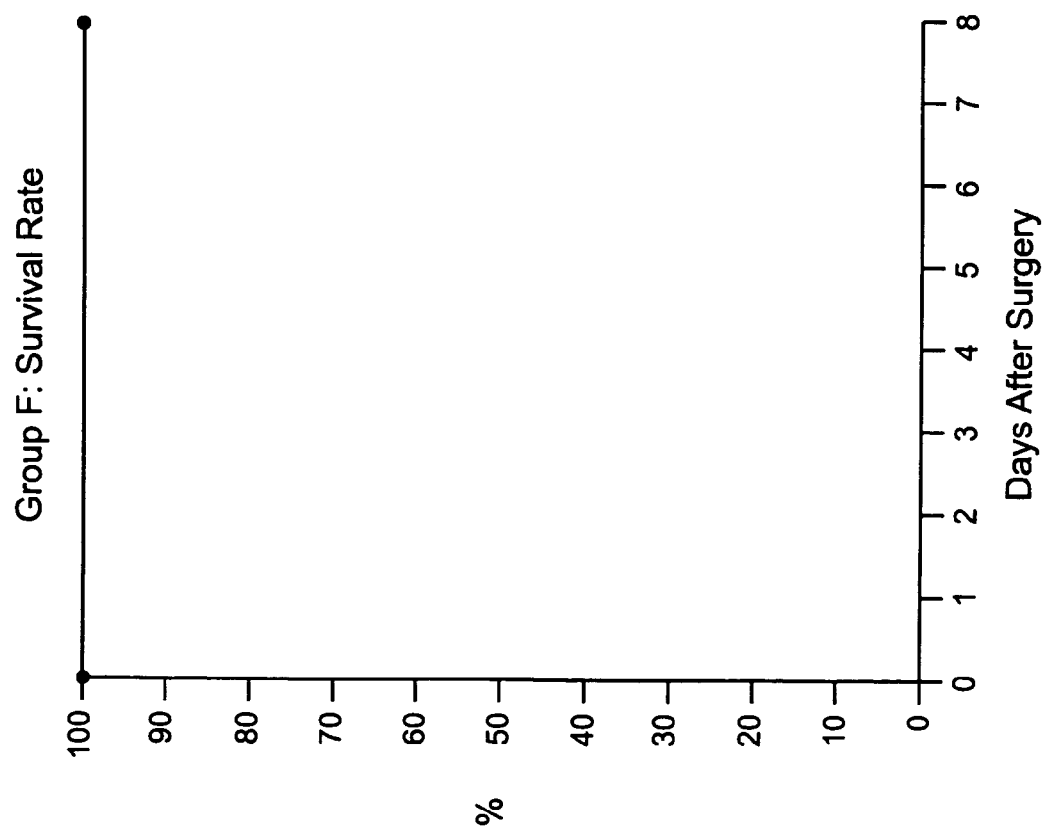
FIG._5

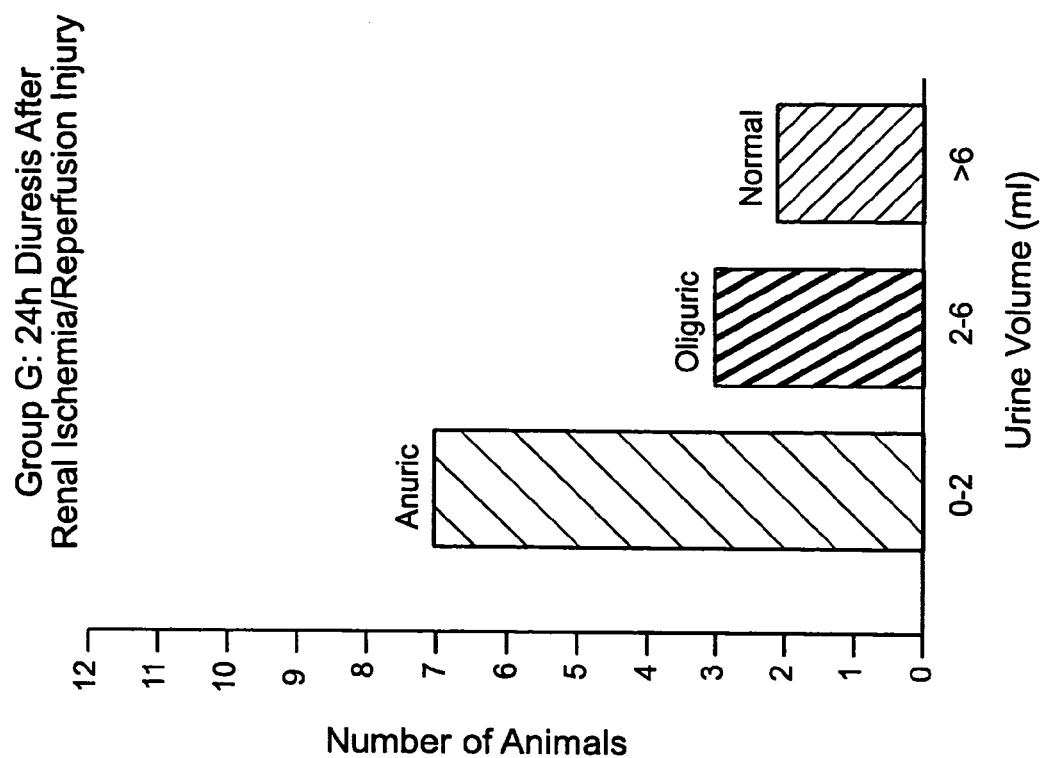
FIG._8
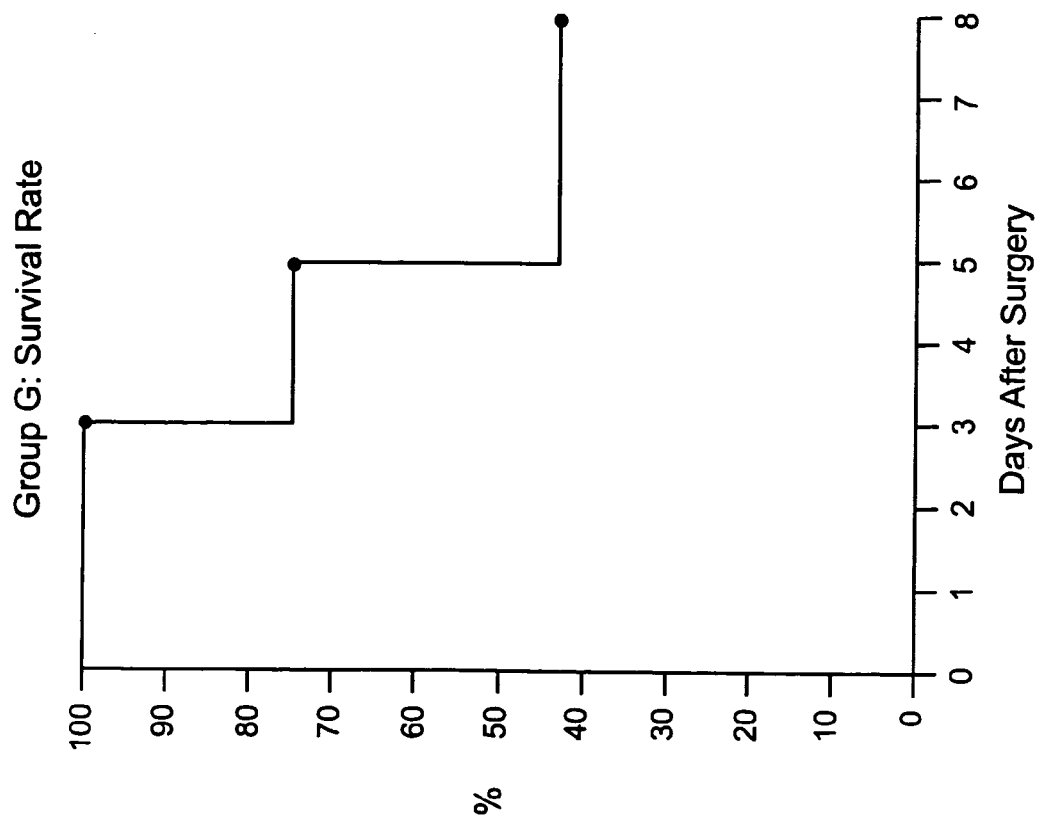
FIG._7

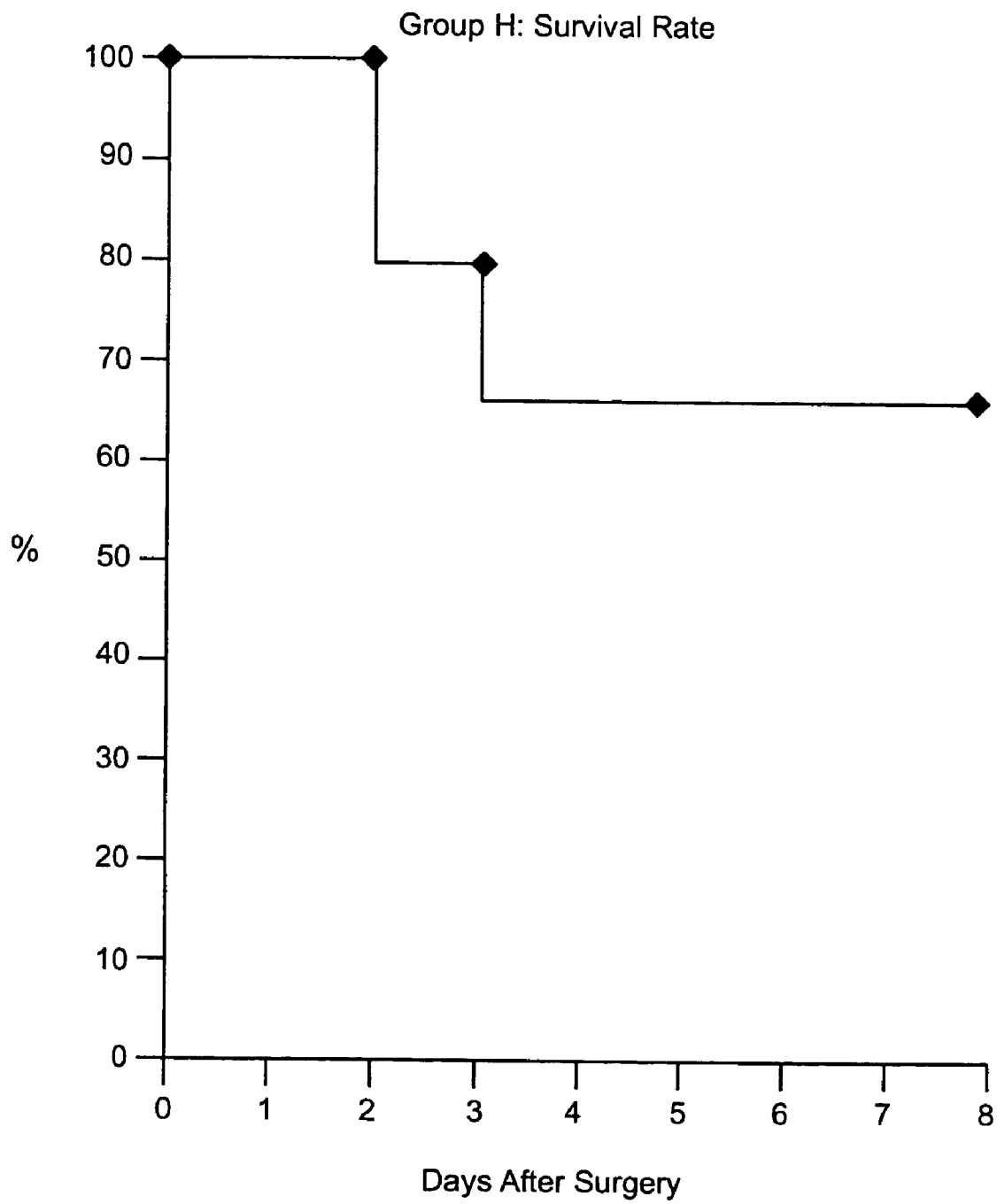
FIG._9

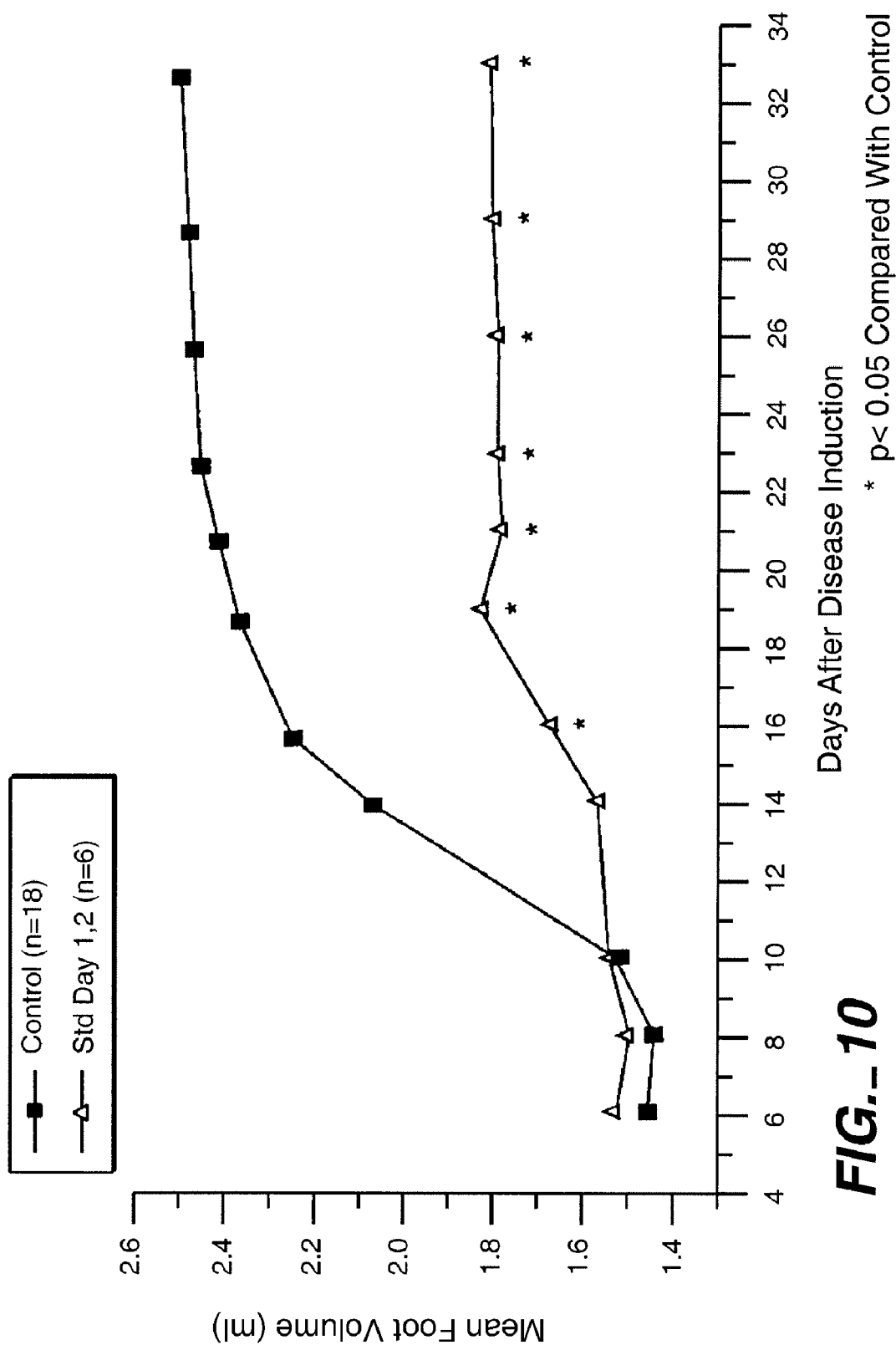
FIG._10 ative environment, UV light and elevated temperature up to about 45° C. This application discloses various treatment methods. Examples 1 and 3 disclose a single course of treatment comprising ten injections administered over a period of 10 days; and Examples 4 and 6 to 8 disclose a treatment method comprising two courses of treatment, each comprising ten injections administered over a period of 10 days, separated by a rest period of about three weeks.

METHOD FOR TREATING MAMMALS WITH MODIFIED MAMMALIAN BLOOD

This application is a continuation of U. S. patent application Ser. No. 09/564,853 filed on May 5, 2000 now U. S. Pat. No. 6,986,888, which claims priority to Canadian Patent Application No. 2,2171,190, filed on May 6, 1999, all of which applications are incorporated herein by reference in their entireties.

FIELD OF THE INVENTION

This invention relates to the field of medicine and medical treatments. In particular, the invention relates to improved methods for treating the mammalian body, including the human body, by administration thereto of modified mammalian blood.

BACKGROUND OF THE INVENTION

Mammalian blood modified by exposure to one or more certain stressors has been found useful for the treatment and prevention of a wide variety of pathological conditions. The stressors to which the blood is exposed are selected from one or more of an oxidative environment, a temperature stressor and ultraviolet (UV) light. The following is a brief discussion of the prior art relating to uses of mammalian blood which has been modified by one or more of the above-mentioned stressors.

U.S. Pat. No. 4,968,483 to Mueller et al. describes an apparatus for oxygenating blood by treating an aliquot of a patient's blood extracorporeally, with an oxygen/ozone mixture and UV light, at a controlled temperature. The apparatus taught by Mueller is proposed for use in hematological oxidation therapy.

U.S. Pat. No. 5,591,457 to Bolton discloses a method of inhibiting the aggregation of blood platelets in a human, a method of stimulating the immune system and a method of treating peripheral vascular diseases such as Raynaud's disease, by extracting an aliquot of blood from a patient, subjecting it to an ozone/oxygen gas mixture and UV light at a temperature in the range of about 37 to 43° C., and then re-injecting the treated blood in the human patient.

U.S. Pat. No. 5,834,030 to Bolton describes a similar process for increasing the content of nitric oxide in the blood of mammalian subject, potentially useful in treating conditions such as high blood pressure in mammalian subjects. Example 5 of this patent discloses a course of treatment comprising ten injections of modified mammalian blood administered over a period of 2 to 4 weeks.

International Publication No. WO 98/07436 describes an autoimmune vaccine for administration to human patients to alleviate the symptoms of autoimmune diseases such as rheumatoid arthritis. The vaccine comprises an aliquot of the subject's blood which has been subjected extracorporeally to an oxidizing environment, UV light and elevated temperature. This application discloses a course of treatment comprising from 30 to 60 injections of modified mammalian blood.

International Publication No. WO 96/34613 relates to treatment of vascular disorders associated with deficient endothelial function, in a mammalian subject, by administration to the patient of an aliquot of blood which has been modified by having been subjected to at least one stressor selected from elevated temperature in the range of 37° to 55° C., UV light and an oxidative environment. This application discloses a number of different treatment methods. For example, Example 1 discloses ten injections of modified mammalian blood administered over a period of 2 weeks; Example 2 discloses ten injections over a period of 2 to 4 weeks; Example 3 discloses a treatment schedule comprising two courses of treatment, the first course comprising ten injections over a period of 2 to 4 weeks and the second course comprising five injections; and Example 5 discloses administration of five injections at 2 to 3 day intervals.

U.S. patent application Ser. No. 09/190,236, filed Nov. 13, 1998, describes a method for lowering levels of lipids in mammals by injecting a mammalian subject with an aliquot of mammalian blood which has been treated extracorporeally by one or more stressors selected from heat, UV light and oxidative environments. This application describes a study in which animals were subjected to a course of treatment comprising a total of 10 injections over 12 days, with two sets of 5 daily injections being separated by a rest period of two days.

U.S. patent application Ser. No. 09/151,653, filed Nov. 9, 1998, discloses a method for treatment of stress and pre-conditioning against stress by injecting a mammalian subject with an aliquot of mammalian blood having been subjected extracorporeally to at least one stressor selected from an oxidative environment, UV light and elevated temperature up to about 45° C. This application discloses various treatment methods. Examples 1 and 3 disclose a single course of treatment comprising ten injections administered over a period of 10 days; and Examples 4 and 6 to 8 disclose a treatment method comprising two courses of treatment, each comprising ten injections administered over a period of 10 days, separated by a rest period of about three weeks.

Although the treatments described above have been shown to be useful in the treatment and prevention of a wide range of pathological conditions, there is a desire to develop a treatment schedule which is less costly to administer and more convenient to patients, and which either improves or at least does not reduce the effectiveness of the treatment.

SUMMARY OF THE INVENTION

The present invention provides a novel method of treating a mammalian subject with modified mammalian blood which provides advantages over previously known methods of treatment, which have typically required subjects to be treated with a relatively large number of injections of modified blood.

The present invention is based upon the discovery that an effective treatment may be provided in which the number of aliquots of modified blood administered to the mammalian subject is substantially reduced from that disclosed in the prior art, while the efficacy of the treatment is significantly enhanced.

Accordingly, in one aspect, the present invention provides a method of treatment or prophylaxis of a condition in a mammalian subject in which modified mammalian blood is administered to said subject, said blood being modified extracorporeally by exposure to at least one stressor selected from the group consisting of an oxidative environment, an electromagnetic emission and a temperature above or below body temperature, said method comprising: administering to said subject from two to four aliquots of said modified mammalian blood, with the administration of any pair of consecutive aliquots either being on consecutive days or being separated by a rest period of 1 to 21 days on which no aliquots are administered to the subject; the rest period preferably being from about 3 to about 15 days.

The modified aliquot of blood is preferably prepared by exposing it to one or more stressors selected from an oxidative stressor, a temperature stressor and an electromagnetic emission, alone or in combinations of two or three of such stressors, applied simultaneously or sequentially.

BRIEF DESCRIPTION OF THE DRAWINGS

The invention will now be more frilly described, by way of example only, with reference to the accompanying drawings.

FIG. 1 is a graph showing the survival rate of rats indicated as the number of days following surgery to induce ischemia/reperfusion injury versus percentage of survival rate of the rats, where the rats received injection of modified blood on days 1 and 21.

FIG. 2 is a graph showing the urine volume (ml) in rats 24 hours after renal ischemial/reperfusion injury was surgically induced, where the rats received injection of modified blood on days 1 and 21.

FIG. 3 is a graph showing the survival rate of rats indicated as the number of days following surgery to induce ischemia/reperfusion injury versus percentage survival rate of the rats, where the rats received injection of modified blood on day 1, followed by a five day rest period, and a second injection of modified blood on day 7.

FIG. 4 is a graph showing the urine volume (ml) in rats 24 hours after renal ischemia/reperfusion injury was surgically induced, where the rats received injection of modified blood on day 1, followed by a five day rest period, and a second injection of modified blood on day 7.

FIG. 5 is a graph showing the survival rate of rats indicated as the number of days following surgery to induce ischemia/reperfusion injury versus percentage survival rate of the rats, where the rats received injection of modified blood on day 1 and day 2, followed by a rest period of 11 days, and a third injection of modified blood on day 14.

FIG. 6 is a graph showing the urine volume (ml) in rats 24 hours after renal ischemial/reperfusion injury was surgically induced, where the rats received injection of modified blood on day 1 and day 2, followed by a rest period of 11 days,and a third injection of modified blood on day 14.

FIG. 7 is a graph showing the survival rate of rats indicated as the number of days following surgery to induce ischemia/reperfusion injury versus Percentage survival rate of the rats, where the rats received an injection of saline on days 1 and 21.

FIG. 8 is a graph showing the urine volume (ml) in rats 24 hours after renal ischemia/reperfusion injury was surgically induced, where the rats received an injection of saline on days 1 and 21.

FIG. 9 is a graph showing the survival rate of rats indicated as the number of days following surgery to induce ischemia/reperfusion injury versus percentage survival rate of the rats, where the rats received injection of treated blood on day 1, followed by a rest period of 12 days, and a second injection of treated blood on day 14.

FIG. 10 is a graph showing the number of days following the induction of arthritis and mean foot volume in the control group (saline) in the test group.

DETAILED DESCRIPTION OF PREFERRED EMBODIMENTS

According to a preferred process of the present invention, an aliquot of blood is extracted from a mammalian subject, preferably a human, and the aliquot of blood is treated ex vivo with certain stressors, described in more detail below. The terms "aliquot", "aliquot of blood" or similar terms used herein include whole blood, separated cellular fractions of the blood including platelets, separated noncellular fractions of the blood including plasma, plasma components, and combinations thereof. The effect of the stressors is to modify the blood, and/or the cellular or non-cellular fractions thereof, contained in the aliquot. The modified aliquot is then re-introduced into the subject's body by any suitable method, most preferably intramuscular injection, but also including subcutaneous injection, intraperitoneal injection, intra-arterial injection, intravenous injection and oral, nasal or rectal administration.

The stressors to which the aliquot of blood is subjected ex vivo according to the method of the present invention are selected from temperature stress (blood temperature above or below body temperature), an oxidative environment and an electromagnetic emission, individually or in any combination, simultaneously or sequentially. Suitably, in human patients, the aliquot has a sufficient volume that, when re-introduced into the patient's body, has the desired effect. Preferably, the volume of the aliquot is up to about 400 ml, preferably from about 0.1 to about 100 ml, more preferably from about 5 to about 15 ml, even more preferably from about 8 to about 12 ml, and most preferably about 10 ml.

It is preferred, according to the invention, to apply all three of the aforementioned stressors simultaneously to the aliquot under treatment, in order to ensure the appropriate modification to the blood. It may also be preferred in some embodiments of the invention to apply any two of the above stressors, for example to apply temperature stress and oxidative stress, temperature stress and an electromagnetic emission, or an electromagnetic emission and oxidative stress. Care must be taken to utilize an appropriate level of the stressors to thereby effectively modify the blood to achieve the desired effect.

The temperature stressor warms the aliquot being treated to a temperature above normal body temperature or cools the aliquot below normal body temperature. The temperature is selected so that the temperature stressor does not cause excessive hemolysis in the blood contained in the aliquot and so that, when the treated aliquot is injected into a subject, the desired effect will be achieved. Preferably, the temperature stressor is applied so that the temperature of all or a part of the aliquot is up to about 55° C., and more preferably in the range of from about −5° C. to about 55° C.

In some preferred embodiments of the invention, the temperature of the aliquot is raised above normal body temperature, such that the mean temperature of the aliquot does not exceed a temperature of about 55° C., more preferably from about 40° C. to about 50° C., even more preferably from about 40° C. to about 44° C., and most preferably about 42.5±1° C.

In other preferred embodiments, the aliquot is cooled below normal body temperature such that the mean temperature of the aliquot is within the range of from about −5° C. to about 36.5° C., even more preferably from about 10° C. to about 30° C., and even more preferably from about 15° C. to about 25° C.

The oxidative environment stressor can be the application to the aliquot of solid, liquid or gaseous oxidizing agents. Preferably, it involves exposing the aliquot to a mixture of medical grade oxygen and ozone gas, most preferably by bubbling through the aliquot, at the aforementioned temperature range, a stream of medical grade oxygen gas having ozone as a minor component therein. The ozone content of the gas stream and the flow rate of the gas stream are preferably selected such that the amount of ozone introduced to the blood aliquot, either on its own or in combination with other stressors, does not give rise to excessive levels of cell damage such that the treatment is rendered ineffective. Suitably, the gas stream has an ozone content of up to about 300 µg/ml, preferably up to about 100 µg/ml, more preferably about 30 µg/ml, even more preferably up to about 20 µg/ml, particularly preferably from about 10 µg/ml to about 20 µg/ml, and most preferably about 14.5±1.0 µg/ml. The gas stream is suitably supplied to the aliquot at a rate of up to about 2.0 liters/min, preferably up to about 0.5 liters/min, more preferably up to about 0.4 liters/min, even more preferably up to about 0.33 liters/min, and most preferably about 0.24±0.024 liters/min. The lower limit of the flow rate of the gas stream is preferably not lower than 0.01 liters/min, more preferably not lower than 0.1 liters/min, and even more preferably not lower than 0.2 liters/min.

The electromagnetic emission stressor is suitably applied by irradiating the aliquot under treatment from a source of an electromagnetic emission while the aliquot is maintained at the aforementioned temperature and/or while the oxygen/ozone gaseous mixture is being bubbled through the aliquot. Preferred electromagnetic emissions are selected from photonic radiation, more preferably ultraviolet (UV), visible and infrared light, and even more preferably UV light. The most preferred sources of UV light are UV lamps emitting primarily UV-C band wavelengths, i.e. wavelengths shorter than about 280 nm. Such lamps may also emit amounts of visible and infrared light. Sources of UV light corresponding to standard UV-A (wavelengths from about 315 to about 400 nm) and LW-B (wavelengths from about 280 to about 315) can also be used. For example, an appropriate dosage of such UV light, applied simultaneously with one or both of the aforementioned temperature and oxidative environment stressors, can be obtained from up to eight lamps arranged to surround the sample container holding the aliquot, operated at an intensity to deliver a total LW light energy at the surface of the blood of from about 0.025 to about 10 joules/cm$^2$, preferably from about 0.1 to about 3.0 joules/cm$^2$. Preferably, four such lamps are used.

The time for which the aliquot is subjected to the stressors is normally within the time range of up to about 60 minutes. The time depends to some extent upon the chosen intensity of the electromagnetic emission, the temperature, the concentration of the oxidizing agent and the rate at which it is supplied to the aliquot. Some experimentation to establish optimum times may be necessary on the part of the operator, once the other stressor levels have been set. Under most stressor conditions, preferred times will be in the approximate range of from about 2 to about 5 minutes, more preferably about 3 minutes. The starting blood temperature, and the rate at which it can be warmed or cooled to a predetermined temperature, tends to vary from subject to subject. Such a treatment provides a modified blood aliquot which is ready for injection into the subject.

In one preferred embodiment of the present invention, the aliquot of blood is stressed by being simultaneously subjected to all three of the above stressors using an apparatus of the type described in aforementioned U.S. Pat. No. 4,968,483, issued on Nov. 6, 1990 to Mueller. The aliquot is placed in a suitable, sterile, UV light-transmissive container, which is fitted into the machine. The UV lamps are switched on for a fixed period before the gas flow is applied to the aliquot providing the oxidative stress, to allow the output of the UV lamps to stabilize. The UV lamps are typically on while the temperature of the aliquot is adjusted to the predetermined value, e.g. 42.5±1° C. Then the oxygen/ozone gas mixture, of known composition and controlled flow rate, is applied to the aliquot, for the predetermined duration of up to about 60 minutes, preferably 2 to 5 minutes and most preferably about 3 minutes as discussed above, so that the aliquot experiences all three stressors simultaneously. In this way, blood is appropriately modified according to the present invention to achieve the desired effects.

In the preferred method of the invention, each course of treatment comprises the administration to a mammalian subject of from two to four aliquots of mammalian blood which has been modified as discussed above.

For optimum effectiveness of the treatment, it is preferred that no more than one aliquot of modified blood be administered to the subject per day. In some preferred embodiments of the invention, at least one rest period is provided during the course of treatment. As used herein, the term "rest period" is defined as the number of days between consecutive aliquots on which no aliquots of modified blood are administered to the subject. The maximum rest period between any two consecutive aliquots during the course of treatment is preferably no greater than about 21 days, and is more preferably from about 3 to about 15 days.

In some preferred embodiments, aliquots of modified blood are administered to the subject on consecutive days, i.e. without an intervening rest period. Some preferred embodiments of the invention (comprising administration of 3 or 4 aliquots) include administration of a pair of aliquots on consecutive days and also provide for a rest period between a pair of consecutive aliquots.

More preferably, a course of treatment comprises administration of two or three aliquots to the subject, the course of treatment optionally including at least one rest period, with the longer (in the case of three aliquots) or the only (in the case of two aliquots) rest period between consecutively administered aliquots being from about 5 to 15 days.

Where the course of treatment comprises the administration of two aliquots to the subject, it is most preferred that the aliquots be administered on consecutive days without an intervening rest period.

Where the course of treatment comprises the administration of three aliquots to the subject, it may be preferred to provide two rest periods, including a longer rest period having a length of 9 to 13 days, more preferably about 10 to 12 days, and most preferably about 11 days; and a shorter rest period of 1 to 3 days.

However, where the course of treatment comprises three injections, it is most preferred to administer two of the three aliquots on consecutive days, and also to provide a rest period between two aliquots having a length of 9 to 13 days, more preferably about 10 to 12 days, and most preferably about 11 days. In a particularly preferred example, the first and second aliquots are administered on consecutive days without an intervening rest period, and the second and third aliquots are separated by a rest period of 11 days.

Although it may be sufficient to administer only one course of treatment as described above to the subject, it may be preferred in some circumstances to administer two or more courses of treatment, or to follow the above-described course of treatment by periodic "booster" treatments, if necessary, to maintain the desired effects of the present invention. In particular, it may be preferred to administer booster treatments or to administer a second course of treatments to the subject following a time period of several weeks or months. For example, it may be preferred to provide a time period of from about 1 to about 4 months between consecutive courses of treatment, with 6 weeks being particularly preferred in some embodiments of the invention.

In one preferred embodiment, it is preferred to administer a first course of therapy comprising three injections, with the first and second aliquots being administered on consecutive days without an intervening rest period, and the second and third aliquots are separated by a rest period of 11 days. Following a period of six weeks from the end of the first course of therapy, an identical second course of therapy is administered to the subject.

The invention is further illustrated and described with reference to the following specific examples, comprising animal studies conducted in an approved manner.

In following Examples 1 to 5, the beneficial effects of the present invention are demonstrated in vivo by clinical experiments on juvenile and adult rats, specifically rats of an inbred stream of genetically hypertensive rats (SHR's). These genetically hypertensive rats are the most widely used animal model for hypertension research, and are well known and readily available to researchers in this field. SHR's have several genetic defects, one of the most important being failure to produce appropriate amounts of heat shock proteins when subjected to stress. SHR's develop hypertension rapidly and exhibit exaggerated increases in heart rate, blood pressure and body temperature in response to stress. They represent a model of hypersensitivity to stress. The results obtained using SHR's provide reliable indications of potential results obtainable with human patients.

EXAMPLE 1

Blood from sacrificed SHR's of the same strain as the test animals was collected, treated with sodium citrate anticoagulant and cooled. A portion of the blood was then placed in a sterile container, and subjected simultaneously to UV light, an ozone/oxygen gas oxidative environment and elevated temperature stressors, in an apparatus as generally described in the above-mentioned Mueller patent. More specifically, the blood sample in the sterile, UV-transparent container was heated using infrared lamps to 42.5° C., and while maintained at that temperature, was subjected to UV light emitting UV-C band wavelengths under the preferred conditions previously described. Simultaneously, a gaseous mixture of medical grade oxygen and ozone, the mixture having an ozone content of 13.5 to 15.5 µg/ml, was bubbled through the blood sample at a flow rate of about 240 ml/min. The time of simultaneous UV exposure and gas mixture feed was 3 minutes.

To provide a control, a sterile aqueous physiological saline solution was also prepared.

A total of 60 seven week old SHR's were selected and divided into five groups, Groups A, E, F, G and H, each containing 12 animals. For a period of 10 days (at 7 to 9 weeks of age), each animal of Group A received a daily intragluteal injection of 150 µl of the UV, heat and ozone treated blood, followed by a rest period of 21 days. After the rest period, the animals were subjected to a second series of 10 daily injections of the modified blood, each injection having a volume of 150 µl.

One day following the second course of injections, the rats of Group A were anesthetized under light gas anesthesia, and the right kidney of each animal was removed through a back incision. An occlusive clip was placed on the remaining renal artery and vein to expose the left kidney to transient ischemia, for 60 minutes. Following the exposure to ischemia, the skin was definitively closed. The animals were then followed with respect to the degree of injury resulting from the ischemia and/or the subsequent reperfusion by determining survival rates and by observing the urine output of the animals, which is a measure of renal function.

The survival rate was monitored by daily count of survivors, and is graphically represented in FIG. 1. After eight days, 58% (7 animals) of the sub-group A animals which had received the treated blood injections were surviving. FIG. 2 illustrates that 5 animals were anuric, meaning that they produced less than 2 ml of urine in the 24 hour period following surgery.

EXAMPLE 2

The twelve animals of Group E were treated as discussed above in Example 1, with the exception that the course of therapy comprised a single course of treatment, each comprising two injections separated by a 5 day rest period (i.e. injection on day 1, followed by a five day rest period, followed by an injection on day 7).

Ischemia was induced one day following the final injection as described in Example 1 in the Group E animals, and the results are shown in FIGS. 3 and 4. Specifically, FIG. 3 shows that after 8 days following surgery, 67% (8 animals) of the Group E animals were surviving, and FIG. 4 illustrates that only 4 of the animals of Group E were anuric.

EXAMPLE 3

The Group F animals were treated as set out in Example 1, with the exception that the course of treatment comprised a total of three injections, with the first two injections being administered on consecutive days, with 11 days rest separating the second and third injections (i.e. injections on days 1 and 2, 11 day rest period, injection on day 14).

Ischemia was induced one day following the final injection in the Group F animals as described above in Example 1, with the results being shown in FIGS. 5 and 6. FIG. 5 illustrates a significant increase in survival rate, with 100% of the animals surviving eight days after the surgery. In addition, only 3 of the animals of Group F were shown to be anuric in the 24 hour period following surgery.

EXAMPLE 4

The animals of Group G received injections of physiological saline in place of modified blood, following an injection schedule identical to that in Example 1. Ischemia was induced one day following the final injection as described above in Example 1, and the results are shown in FIGS. 7 and 8. Only 42% (5 animals) of the Group G animals were surviving 8 days after the surgery, and 7 of the animals were shown to be anuric in the 24 hour period following surgery.

EXAMPLE 5

The animals in Group H were treated with a single course of treatment, comprising two injections separated by a 12 day rest period (i.e. injection on day 1, 12 day rest period, injection on day 14). The results of the ischemic stress on the animals of Group H are illustrated in FIG. 9, which illustrates that 67% (8 animals) in Group H were surviving eight days after the surgery. Also, 3 of the animals in Group H were anuric in the 24 hour period following surgery.

The results of the above animal studies are tabulated below.

TABLE I

| Group | # of Courses | # of Injections | Rest Period (Days) | Survival Rate After 8 Days | # of Anuric Animals |
|---|---|---|---|---|---|
| A | 2 | 10 + 10 | 21 | 58% | 5 |
| E | 1 | 1 + 1 | 5 | 67% | 4 |
| F | 1 | 2 + 1 | 11 | 100% | 3 |
| G* | 2 | 10 + 10 | 21 | 42% | 7 |
| H | 1 | 1 + 1 | 12 | 67% | 3 |

*Saline Control

The above results demonstrate that the method of the present invention protects the kidney from injury resulting from ischemia and/or reperfusion, as measured by survival rate and urine flow in the 24 hours following surgery in the SHR. This indicates use of the procedure in protecting other body organs from ischemia/reperfusion injury, including the heart, the liver, the brain, the spinal cord and other vital organs, and indicates practical application of the procedure on patients scheduled to undergo surgical procedures involving ischemia/reperfusion of a body organ, such as surgical repair, removal or transplantation of a body organ.

In particular, ischemic acute renal failure is an important clinical problem with high morbidity and high mortality. The process of the present invention presents a novel approach to combatting this disorder. It can be adopted prior to kidney transplantation, on either or both the donor or recipient. It can be adopted prior to kidney revascularization. It can be adopted prior to invasive evaluation in high risk subjects, e.g. angiography in diabetics. It can be adopted prior to abdominal aortic surgery such as aortic aneurism repair and renal bench surgery (i.e. where the kidney is temporarily removed and operated on ex vivo, and then re-implanted).

As regards its use in connection with procedures involving the heart, the procedure of the invention can be conducted prior to coronary angioplasty, and bypass, or prior to transplantation, as in the case of the kidney. It is indicated for use with patients about to undergo open heart surgery with cardio-pulmonary bypass for coronary artery bypass grafting, valve replacement or surgical repair of congenital or acquired cardiac structural abnormalities. In the case of the brain or other vital organs and tissues including the intestines, the kidneys and limbs, the procedure of the invention can be used prior to angioplasty or endarterectomy, in high risk subjects.

In connection with body organs destined for transplantation, treatment of the donor body by the process of the present invention serves to protect body organs against damage resulting from the inevitable ischemia which the organ will suffer on removal from the donor body, transportation and subsequent surgical introduction into the recipient body. The treatment according to the invention extends the useful life of the transplant organ between its removal from the donor body and its surgical introduction into the recipient body, thereby reducing losses of viable transplant organs due to transportation delays.

The use of the process of the present invention prior to general anaesthesia in connection with major surgery can be viewed as general pre-conditioning of the body, to better withstand ischemia-reperfusion injuries to which the major organs will later be subjected. It is indicated for use prior to conducting major surgical procedures involving general anaesthesia in patients known to have or likely to have a significant degree of underlying atherosclerosis in the arteries supplying the brain, heart, liver, intestine, spinal cord, kidneys or limbs, the atherosclerosis rendering them more susceptible to a thrombo-ischemic event in the operative or post-operative period. In addition, it is known that repetitive mild ischemic (anginal) episodes can render tissues and organs less susceptible to stress-induced damage, by ischemic preconditioning, although application of ischemic preconditioning by current methods is largely impractical. The process of the present invention can take the place of ischemic preconditioning, ischemia being a species of physical stress. Accordingly, the process of the present invention offers potential for treatment of unstable angina and decrease of infarct size, a treatment not effectively addressed by available therapies.

A further, specific clinical application of the process of the invention is in treatment of patients suffering from transient ischemic attacks (TIA's, pre-strokes), which are due to temporary obstruction of blood flow to certain areas of the brain. They commonly indicate the likelihood of suffering a major stroke in the near future. Subjection of such patients to treatment according to the process of the invention, at the onset of TIA's, will precondition the brain to avoid or at least to lessen the severity of the effects of the forthcoming major stroke.

Similar general pre-conditioning of the body by the process of the invention is also indicated for use in alleviating the effects of subsequently encountered shock, leading to under-perfusion of vital organs and tissues through failure of cardiac action due to loss of blood or other body fluids, excessive dilation of blood vessels and excessively low blood pressure. Examples include major blood loss, trauma, sepsis and cardiogenic shock. Individuals likely to be exposed to such hazards, including patients awaiting surgery, rescue and relief crews for natural disasters, would be beneficiaries of the process of the invention.

It now appears that common physiological events underlie all stress responses, including responses to ischemic stresses. These physiological events include the induction and upregulation or synthesis, in all body cells, of a group of specialized intracellular proteins known as heat stress proteins or heat shock proteins (HSP's). These HSPs function to protect the cells from potential damage caused by whatever form of stress is being applied. Therefore, it is expected that the method of the present invention is of general application and will be effective to provide a subject with resistance to a wide variety of different types of stresses, whether evident at the time the treatment is administered, or whether subsequently encountered. For example, psychological stresses induced by restraint, confinement, sudden exposure to danger, shock and the like translate into physical stresses affecting one or more organs of the body. Similarly, physical stress such as exposure to heat or cold, over-exertion and the like, result in abnormal functioning of body organs.

A subject who has undergone a treatment according to the method of the present invention will exhibit notably reduced adverse reactions to subsequently encountered stress, such as a notably reduced rise in body temperature, a reduced increase in heart rate and/or a reduced increase in diastolic blood pressure in response to stress, as compared to a similar but untreated subject.

In addition, it is expected that the improved results obtained by using the process of the invention would also be applicable to other conditions which may be treated by administration to a subject of modified mammalian blood, such as those discussed above with reference to the prior art.

Specific examples of such conditions are diseases of the circulatory system caused by atherosclerosis, for example coronary artery disease, cerebrovascular disease, peripheral vascular disease and diseases of other vascular systems; vasospastic disorders including primary and secondary Raynaud's disease, cardiac syndrome X (microvascular angina), migraine headache, cluster headache, hypertension, pre-eclampsia, and thrombotic disorders related to increased platelet aggregation and/or coagulation abnormalities and/or related endothelial dysfunction; immune system disorders such as rheumatoid arthritis, asthma, graft-versus-host disease, diabetes mellitus, organ rejection, miscarriage, systemic lupus erythematosus, atopic allergy, multiple sclerosis, allergic dermatitis, inflammatory bowel disease and psoriasis.

EXAMPLE 6

Model:

The purpose of the experiment is to determine the effects of treatment according the present invention on the development of atherosclerosis in the LDL receptor (LDL-R) deficient mouse model, a widely used transgenic atherosclerosis model created by targeted disruption of the LDL receptor. This animal model is analogous to familial hypercholesterolemia, an inherited condition in which a mutation results in complete lack of functional LDL-R. In the human disease, homozygous individuals demonstrate a marked increase in serum cholesterol and develop severe premature atherosclerosis, often succumbing to this disease at an early age. In patients with this disease, currently used lipid lowering agents do not have a significant effect in terms of lowering cholesterol levels.

The LDL-R deficient mouse model shows intolerance to cholesterol feeding and develops widespread atherosclerotic changes which progress to mature fibrous lesions morphologically indistinguishable from established human atherosclerosis. Apart from the defined genetic abnormality causing predisposition to atherosclerosis, this model has the advantage of rapid development of widespread atherosclerosis within 6 to 8 weeks following institution of cholesterol feeding.

Protocol:

LDL-R deficient mice were purchased from Jackson Laboratories. The mice were entered into the study at 22 weeks of age. The mice were maintained on a 12 hour dark/12 hour light cycle with free access to food and water, and were fed a specified diet as follows.

Group A (control)—fed a normal diet;

Group B1—fed a high cholesterol diet as described below for 8 weeks;

Group B2—fed a high cholesterol diet as described below for 12 weeks;

Group C1—fed a high cholesterol diet as described below for 8 weeks, and treated by the preferred method of the present invention as described below at 4 weeks of dietary intervention; and Group C2—fed a high cholesterol diet as described below for 12 weeks, and treated by the preferred method of the present invention as described below at 8 weeks of dietary intervention.

The high cholesterol group were fed a diet containing 1.25% cholesterol, 7.5% cocoa butter, 7.5% casein, and 0.5% sodium cholate. To ensure proper food intake, food consumption and animal weight were monitored on a weekly basis. In previous experiments, it was demonstrated that 8 weeks of feeding with the high cholesterol diet results in substantial atherosclerosis development, particularly in the aortic arch and the descending thoracic aorta.

Treatment:

Animals fed the high cholesterol diet were selected at random to undergo a course of treatment by the preferred method of the invention. The treatments began four or eight weeks after initiation of the study, with each of the animals on the high cholesterol diet receiving a total of 3 treatments (injections on days 1, 2 and 14 of the treatment). Each individual injection administered to the animals treated by the method of the present invention consisted of the collection of 10 ml of blood from genetically compatible donor animals fed on a normal diet, the blood being collected into sodium citrate anticoagulant. In order to collect each 10 ml aliquot of blood, about 1 ml of blood was extracted from each of 10 animals. The blood was extracted by cardiac puncture, with the animals being under full xylazine/ketamine anesthesia during the blood extraction procedure, and being given T-61 immediately following extraction. The blood aliquot was transferred to a sterile, disposable, low-density polyethylene vessel for ex vivo treatment, and was then treated simultaneously with a gaseous oxygen/ozone mixture and ultraviolet light at elevated temperature using an apparatus as generally described in aforementioned U.S. Pat. No. 4,968,483 to Mueller et al.

The constitution of the gas mixture was 14.5±1.0 μg ozone/ml, with the remainder of the mixture comprising medical grade oxygen. The gas mixture was bubbled through the aliquot at a rate of 240±24 ml/min for a period of 3 minutes. The temperature of the aliquot was held steady at 42.5±1.0° C. The UV light was within the UV-C band, and included a wavelength of 253.7 nm.

After treatment by the preferred method of the present invention, 30 μl of the treated blood was re-injected intramuscularly into each animal undergoing treatment according to the present invention. As discussed above, 3 treatments were administered to each animal over a 14 day period, with injections being administered on days 1, 2 and 14.

In the sham treatments, 30 μl of untreated blood was injected intramuscularly into each of the remaining five animals on the high cholesterol diet.

Assessment of Atherosclerosis:

After 8 or 12 weeks, the animals were anesthetized with zylaxine/ketamine and the heart was exposed. After nicking the vena cava to obtain blood samples, the animals were perfused via ventricular puncture, first with PBS to flush out the blood and then with 10% neutral buffered formalin for 3 minutes to fix the aorta. The thoracic aorta was dissected away from the thorax en bloc and stored in 10% formalin at 4° C. Pressure-fixed (10% formalin) aortae were removed en bloc and opened to allow a longitudinal fill length inversion. The aortae were then mounted internally exposed on glass slides and stained with oil red O. The bright red staining (indicating lipid deposition) was then quantified using a computer assisted morphometric system, and expressed as a percentage of total aortic intimal surface.

Statistical Analysis:

Continuous variables are reported as mean± SD. Differences in atherosclerotic lesion area among groups were tested using the one-way ANOVA test in conjunction with the Bonferroni correction.

Results:

As demonstrated by measurement of atherosclerotic area, the animals of group B (high cholesterol diet alone) exhibited substantial aortic lipid deposition, with group B1 animals having atherosclerosis ratios (AA/TA) of 0.16±0.1 at eight weeks and group B2 animals having ratios of 0.17±0.1 at 12 weeks of dietary intervention. In contrast, the animals of group C (high cholesterol diet with treatment according to the invention) exhibited profoundly reduced lipid deposition, with group C1 animals having ratios of 0.04±0.02 (p<0.05) at eight weeks of dietary intervention, and group C2 animals having ratios of 0.04±0.02 (p<0.01) at twelve weeks of dietary intervention.

The animals of group C also exhibited a marked reduction in xanthelasma and limb swelling as compared to animals of group B.

As shown in Example 6, the treatment according to the present invention substantially inhibited the development of atherosclerosis in a mouse model of familial hypercholesterolemia These improvements in cardiovascular health were accompanied by improvements in the animals' general overall appearance and appetite.

EXAMPLE 7

In this example, LDL-R deficient mice were fed a high cholesterol diet as in Example 6 for a period of 12 weeks and divided into two treatment groups, Group I and Group II. All animals of both groups received a first course of treatment comprising injections on days 1, 2 and 14 as described above in Example 6. In addition, the animals of Group II received a second, identical course of treatment 6 weeks after the end of the first course of treatment.

All animals were sacrificed 24 weeks after initiation of the high cholesterol diet. Calculation of percent plaque area by en face examination of oil red O stained aortas revealed a 38% reduction in plaque-area in Group II animals (0.32±0.03% for sham versus 0.20±0.03% for treated, p=0.016) but no reduction in plaque area in the Group I animals.

The above example indicates that in some embodiments of the invention it may be preferred to administer two or more courses of therapy at spaced intervals.

EXAMPLE 8

This example demonstrates the beneficial effects of the present invention in vivo clinical experiments on rats, specifically male Lewis rats in which rheumatoid-like arthritis has been induced. An animal model used for studying rheumatoid arthritis is adjuvant-induced arthritis in a rat model (see, for example, Pearson, C., 1956, "Development of Arthritis, periardritis and periostitis in rats given adjuvant", *Proc. Soc. Exp. Biol. Med.*, 91:95). According to this model, arthritis is induced in rats by injecting them with adjuvant containing *Mycobacterium butyricum*.

Male Lewis rats, 4 to 5 weeks of age, 100 to 120 g, were obtained from Charles River Laboratories, quarantined one week and entered into the study. An adjuvant mixture was prepared for induction of arthritis by suspending 50 mg *M. butyricum* (Difco Laboratories, Inc., Detroit Mich.) in 5 ml light white paraffin oil—m3516 (Sigma Chemical Co., St. Louis, Mo.) and thoroughly mixed using a homogenizer.

Aliquots of the mixture sufficient to supply 0.15 mg *M. butyricum* were injected into each animal subcutaneously, at the base of the tail. Symptoms of arthritis appeared about 12 days after induction, in each animal, as evidenced by limb swelling.

Blood was collected from donor animals, by cardiac puncture. 10 ml of citrated donor blood was transferred to a sterile, low density polyethylene vessel for ex vivo treatment with stressors according to the invention. Using an apparatus as described in the above-mentioned Mueller patent (more specifically, a VasoCare™ V7000 apparatus), the blood was heated to 42.5±1° C. and at that temperature irradiated with ultraviolet light, principally at a wavelength of 254 nm, while a gas mixture of medical grade oxygen containing 14.5±1.0 µg/ml of ozone was bubbled through the blood at a flow rate of 240±24 ml/min.

Six animals were given a course of 2 injections of 0.2 ml aliquots of the treated blood, on days 1 and 2 after disease induction. Eighteen animals were injected with untreated blood or saline as controls. Hind paw volumes and clinical scores of the animals were measured every 2 to 3 days for 5 weeks after disease induction. Hind paw volumes were measured by water displacement in a 250 ml beaker using a top-loaded Mettler balance.

The results of this study showed that the incidence of arthritis in the treated group was decreased as compared with the control group, as measured both by clinical scores and foot volumes. The results of the foot volume measurements for each group of animals were averaged and are presented graphically on the accompanying FIG. 10, a plot of mean foot volume against days after induction of arthritis. The upper curve is derived from the control group of animals, the lower curve from the animals which received the course of injections of treated blood. A significant decrease in the severity of the arthritis, as indicated by lower foot volumes, is apparent for the treated animals as compared to the animals of the control group.

Although the invention has been described in connection with certain preferred embodiments, it is to be appreciated that it is not limited thereto. Rather, the present invention includes within its scope all embodiments which may fall within the scope of the following claims.

What is claimed is:

1. A method for inhibiting injury arising from hypertension or endothelial dysfunction in a mammalian subject which method comprises:
    identifying a mammalian subject at risk of injury from hypertension or endothelial dysfunction;
    administering to said subject three aliquots of said subject's modified blood according to the following regimen:
    a) two aliquots of modified mammalian blood in a volume of about 0.1 ml to 100 ml on consecutive days; and
    b) a third aliquot of modified mammalian blood in a volume of about 0.1 ml to 100 ml, after a rest period of 11 days after administration of the second aliquot,
    wherein said blood is modified extracorporeally by exposure for a period of from about 2 to 5 minutes to a combination of stressors selected from the group consisting of a concentration of ozone from about 10 to 20 µg/ml, UV light at a dosage of from about 0.1 to about 3 Joules/cm$^2$; and heating to a temperature above normal body temperature to about 55° C.

2. The method according to claim 1, wherein said injury arises from hypertension.

3. The method according to claim 1, wherein the injury arises from endothelial dysfunction.

4. A method for inhibiting injury arising from hypertension or endothelial dysfunction in a mammalian subject which method comprises:
   identifying a mammalian subject at risk of injury from hypertension or endothelial dysfunction;
   administering to said subject three aliquots of said subject's modified blood according to the following regimen:
   a) two aliquots of modified mammalian blood in a volume of about 0.1 ml to 100 ml on consecutive days; and
   b) a third aliquot of modified mammalian blood in a volume of about 0.1 ml to 100 ml, after a rest period of 11 days after administration of the second aliquot,
   wherein said blood is modified extracorporeally by exposure for a period of about 3 minutes to a combination of stressors selected from the group consisting of a concentration of ozone from 13.5 to 15.5 µg/ml at a flow rate of about 240 ml/minute, UV light at a dosage of from about 0.1 to about 3 joules/cm$^2$; and a temperature of about 42.5° C.

5. A method for inhibiting injury arising from hypertension or endothelial dysfunction in a mammalian subject which method comprises:
   identifying a mammalian subject at risk of injury of hypertension or endothelial dysfunction;
   administering to said subject three aliquots of said subject's modified blood according to the following regimen:
   a) two aliquots of modified mammalian blood in a volume of about 0.1 ml to 100 ml on consecutive days; and
   b) a third aliquots of modified mammalian blood in a volume of about 0.1 ml to 100 ml, after a rest period of 11 days after administration of the second aliquot,
   wherein said blood is modified extracorporeally by exposure for a period of about 2 to 5 minutes to a combination of stressors selected from the group consisting of a concentration of ozone from about 10 to 20 µg/ml, UV light at a dosage of from about 0.1 to about 3 Joules/cm$^2$; and heating to a temperature from about 40° to about 50° C.

* * * * *